United States Patent [19]

Christmas

[11] Patent Number: 4,490,982
[45] Date of Patent: Jan. 1, 1985

[54] METHOD OF AND APPARATUS FOR THE CONTROLLED COOLING OF A PRODUCT

[75] Inventor: Michael J. Christmas, Worcester Park, England

[73] Assignee: Planer Products Limited, Sunbury-On-Thames, England

[21] Appl. No.: 435,308

[22] Filed: Oct. 19, 1982

[51] Int. Cl.³ .............................................. F25B 21/02
[52] U.S. Cl. .................................................... 62/3
[58] Field of Search ................... 62/3, 467, 62, 378, 62/448

[56] References Cited

U.S. PATENT DOCUMENTS

| | | | |
|---|---|---|---|
| 3,436,924 | 4/1969 | Lawless | 62/3 |
| 4,066,365 | 1/1978 | Staunton | 62/3 X |
| 4,248,259 | 2/1981 | Kaartinen et al. | 62/3 X |
| 4,361,011 | 11/1982 | Callender et al. | 62/3 |

Primary Examiner—Lloyd L. King
Attorney, Agent, or Firm—Young & Thompson

[57] ABSTRACT

For the controlled cooling of specimens which are at least partially of liquid form, especially biological specimens, it is important that crystallization at the freezing point takes place locally, without supercooling, and preferably with absorption of the latent heat of fusion. A cooling device which comprises at least one module which operates in accordance with the Peltier effect, with the "cold" faces of the modules connected by a conductive metal strip, has the specimen container in contact with the strip. The device is mounted in a working chamber which has its temperature/time profile controlled. At a temperature which is a predetermined amount above a given critical temperature for the specimen, e.g. its freezing point, the Peltier effect modules are energized to effect supplementary cooling at a local area, for example one end of the specimen.

22 Claims, 8 Drawing Figures

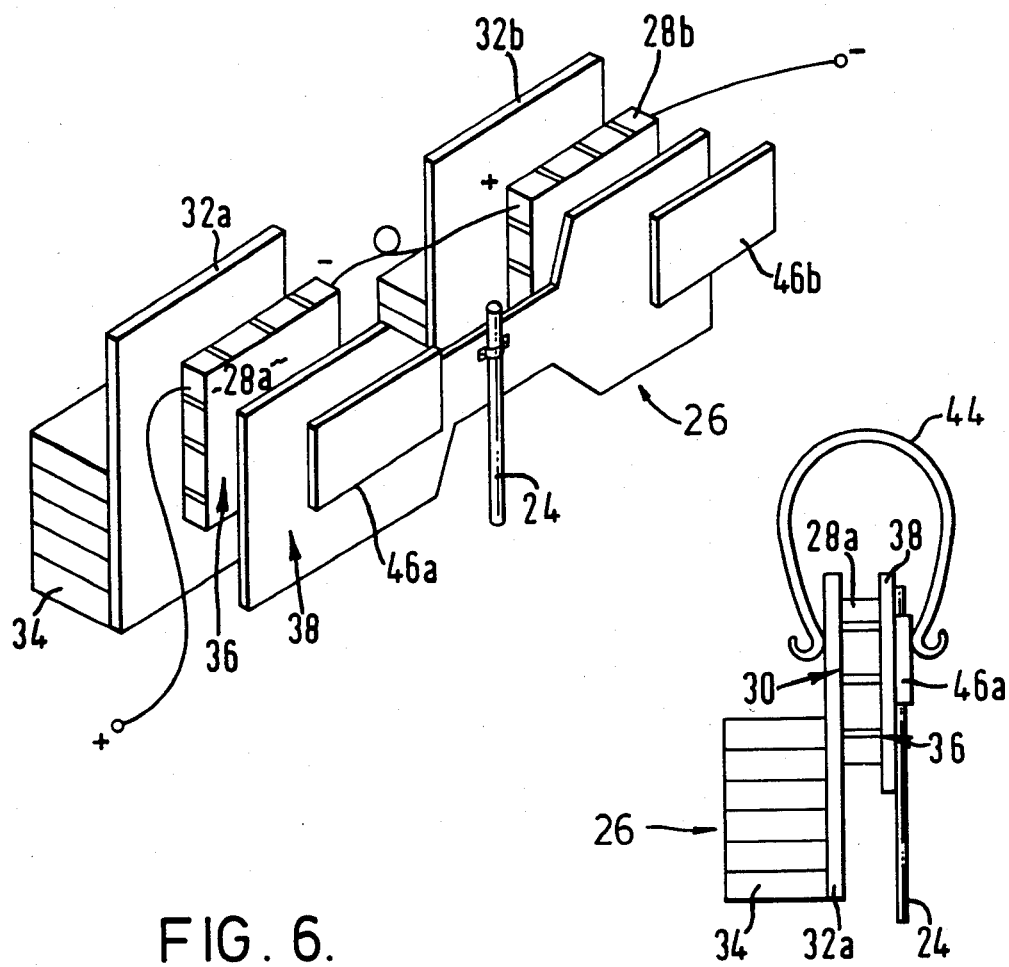
FIG. 5a.
FIG. 5b.
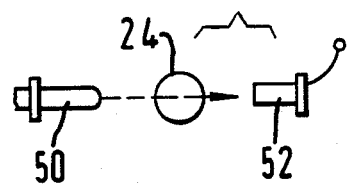
FIG. 6.

METHOD OF AND APPARATUS FOR THE CONTROLLED COOLING OF A PRODUCT

BACKGROUND OF THE INVENTION

This invention relates to methods of and apparatus for the controlled cooling of a product. The invention is particularly concerned with the controlled cooling of specimens which are at least partially in liquid form. One particular application of the invention is to the freezing, e.g. for preservation, of biological materials.

It is well known to freeze biological and other materials, e.g. animal embryos, blood constituents etc., for the purpose of preservation in carrier media. The material is frozen in a liquid carrier medium at an accurately controlled rate, for example by the release of liquid nitrogen or some other coolant which is evaporated in the vicinity of the specimen. Suitable control equipment is used in the admittance of the coolant to maintain the appropriate cooling rate. When biological material is cooled, the critical rate, for instance typically −1° C. per minute is commenced above the freezing point of the solution/suspension. One difficulty encountered in such controlled freezing procedures, for example in the freezing of embryos in liquid nitrogen, results from the sudden crystallisation of constituents of the material to be frozen, for example at temperatures between −7° C. and −16° C. Experience as shown that without special precautions crystallization during cooling takes place effectively simultaneously throughout the body of the specimen, with the resulting "shock" causing damage to the biological material. For this reason it is common practice in such cases to induce crystallization at the upper end of the ampoule or other container for the specimen, by physically contacting the ampoule or container with tongs or some other metal member which has previously been cooled in liquid nitrogen. The local crystallization which is thereby initiated then spreads progressively downwards through the ampoule or container and throughout the body of the specimen. Because this crystallization is more progressive, the survival rate of the biological material is substantially enhanced.

Another problem encountered in such controlled freezing procedures, and this is not limited to biological specimens, is that when crystallisation occurs the laten heat of fusion of the solution/suspension is released and the temperature of the liquid rises. There is also the potential problem of supercooling of the liquid, again with the danger of instant massive crystallization throughout the body of the liquid.

Among the disadvantages of the known methods described above, particularly the use of metal tongs, is the necessity of introducing mechanical movement within the cooling chamber, or in some cases momentary withdrawal of the specimen container, thus creating a risk of upsetting the control of the cooling rate. In addition, such manoeuvres are extremely inconvenient to the operator and require skill and expertise in order to achieve consistent satisfactory results.

SUMMARY OF THE INVENTION

It is the primary object of the present invention to provide a method of and apparatus for modifying the cooling rate of a specimen, which is at least partially in the liquid phase, in a controlled manner. This may be for example to induce crystallisation of the body of liquid at a particular location, or to induce precipitation or sedimentation of material from the liquid, or to absorb the heat of an exothermic reaction.

It is an object of a preferred embodiment of the present invention to provide an improved method of and apparatus for at least partially removing the latent heat of crystallisation of a liquid which is progressively cooled, thereby considerably reducing the temperature rise within the liquid resulting from the latent heat of crystallisation.

Such preferred absorption of the latent heat of crystallisation or fusion is effected either automatically or under manual control without any need for mechanical movement of the specimen or the introduction of a foreign body, such as a pair of cold tongs.

It is yet another object of the present invention to provide a method of and apparatus for modifying the cooling rate of a liquid specimen by means of which one can subject it to short-term supplementary cooling initiated at a predetermined point preferably closer to the freezing point of the liquid than is otherwise practicable. It is advantageous to be able to initiate this supplementary cooling as close to the freezing point as possible, because one then needs less energy input and error is reduced.

In accordance with the present invention there is provided a method of modifying the cooling rate of a specimen which is at least partially of liquid form which comprises the steps of:

(a) cooling the specimen in toto to a temperature level which is close to a given critical temperature, and (b) at said temperature level subjecting the specimen to supplementary cooling by passing an electric current through Peltier effect means in thermal contact with the specimen.

Also in accordance with the invention there is provided a cooling device for modifying the cooling rate of a specimen which is at least partially of liquid form, comprising cooling means arranged to be connected to an electric power source and to function in accordance with the Peltier effect to provide a surface at which heat is absorbed thereby to cool said surface, a container for the specimen in thermal contact with said surface, and control means operative to initiate energisation of said cooling means at a temperature which is close to a given critical temperature for said specimen.

The invention also extends to cooling apparatus comprising such a cooling device, a working chamber within which said cooling device is positioned, means to supply a coolant to said working chamber, and temperature sensing means within said working chamber connected to said control means.

Preferably, the supplementary cooling is effected on a portion only of the specimen. If the specimen is elongated, this may be at one end. The critical temperature may be the freezing point of the liquid, or the temperature at which precipitation or sedimentation occurs.

Although in one embodiment of the present invention one can aim to absorb the latent heat with the Peltier effect means and maintain the controlled flow of general coolant unchanged, it should be understood that the invention also includes a method in which the Peltier effect means is used simply as a trigger, e.g. to initiate seeding, and this is accompanied or followed by a boost in the cooling effected by the external coolant, for example liquid nitrogen, here, the latent heat is not removed, or is only partially removed, from the specimen by the Peltier effect means. One can therefore use smaller Pelter effect devices with such a system.

BRIEF DESCRIPTION OF THE DRAWINGS

In order that the invention may be fully understood various embodiments in accordance with the invention will now be described by way of example and with reference to the accompanying drawings, in which:

FIGS. 5a and 5b are similar perspective and side views of a second embodiment of cooling device in accordance with the invention; and, FIG. 6 is a schematic illustration of an optical device which can be used in conjunction with the apparatus of the present invention.

Figure 1:
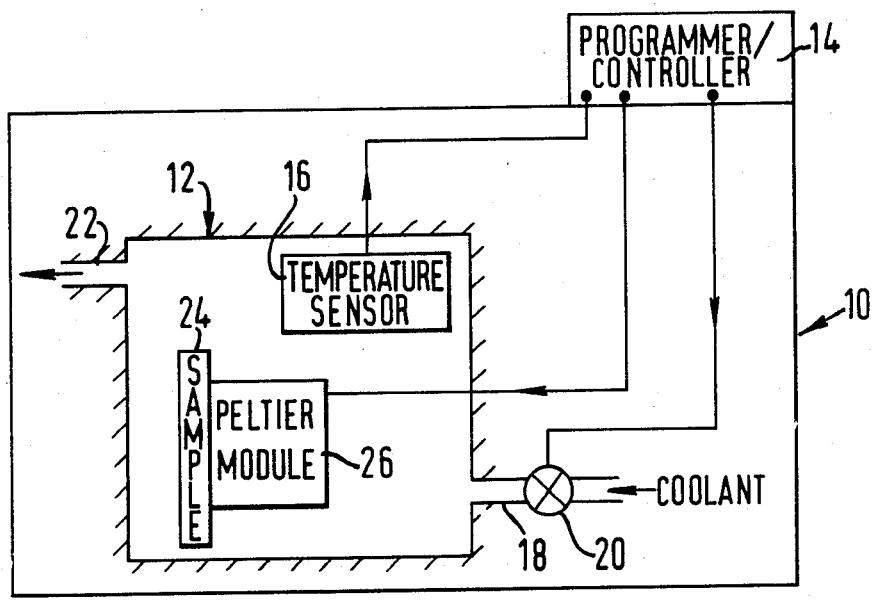
FIG. 1 is a schematic representation of a biological freezer incorporating a working chamber holding a specimen which is arranged to be cooled in a controlled manner in accordance with the present invention.

Referring first to FIG. 1, this shows a freezer 10, for example a conventional biological freezer, which incorporates a working chamber indicated generally at 12. Also provided is a programmer/controller unit 14 which is effective to control the temperature/time profile of the cooling process which takes place within the working chamber 12. For this purpose the programmer/controller unit 14 is connected to a temperature sensor 16, mounted within the working chamber. Connected to the working chamber 12 is a coolant supply pipe 18 which incorporates appropriate control valve means 20. This control valve means 20 is connected to the programmer/controller unit 14. An output pipe 22 is also connected to the working chamber 12. The freezer 10 is a conventional unit and the other component parts, mechanical, electrical and/or electronic, will not therefore be described in detail.

Within the working chamber 12 there is mounted a sample 24. This sample 24 contains the liquid or liquid and solid which is to be treated, for example frozen, and may comprise for example a glass ampoule, a bag or other container, a thick-walled plastics container, a plastics straw, or a metal container. It should be understood that the present invention is appropriate for use with a sample container of any shape or material.

Also mounted within the working chamber 12 is a unit, indicated generally at 26, which is at the heart of the present invention and which comprises a Peltier-effect type cooling device. Two embodiments of such a device are shown in FIGS. 4 and 5 and will be described in more detail later. The Peltier effect is the phenomenon whereby heat is absorbed, or liberated, at a junction where an electric current passes from one metal to another.

Figure 2:
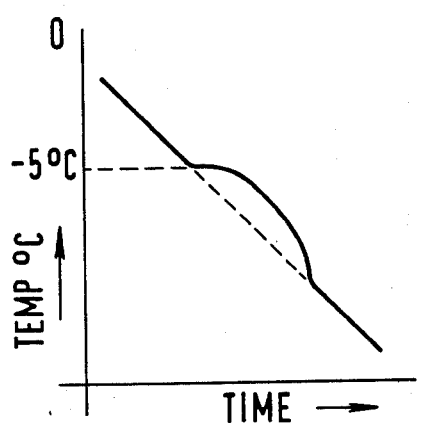
FIG. 2 is a graphical representation showing a typical rise in temperature which occurs in a liquid when it undergoes crystallization.
Figure 3:
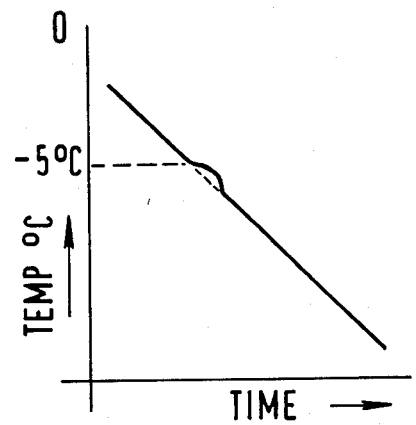
FIG. 3 is a similar graphical representation showing the effect of the use of the method and apparatus of the present invention in reducing the rise in temperature within the specimen.

FIG. 2 illustrates what happens when a liquid, for example a solution or suspension, is cooled through its freezing point. It will be seen that as the temperature falls from 0° C. to −5° C. the cooling curve is linear. At the freezing point, i.e. −5° C., as crystallization occurs, latent heat is generated which delays the further cooling of the liquid and creates an attendant risk of damage to biological specimens. The latent heat of crystallisation has to be absorbed by the gas around the sample 24 within the working chamber 12. In contrast, as shown in FIG. 3, with the method and apparatus of the present invention, one achieves a quite different rate of cooling curve. The curve departs only very slightly from the straight lines because of the much more rapid absorption of the latent heat with the system of the present invention. As will be explained hereinafter, the method and apparatus of the present invention provide local cooling for the sample, either to absorb this latent heat, instead of leaving this to the environmental gas within the chamber, or to initiate a boost in the cooling due to the environmental gas in the case where the local cooling is just used to induce crystal formation.

Figures 4A, 4B:
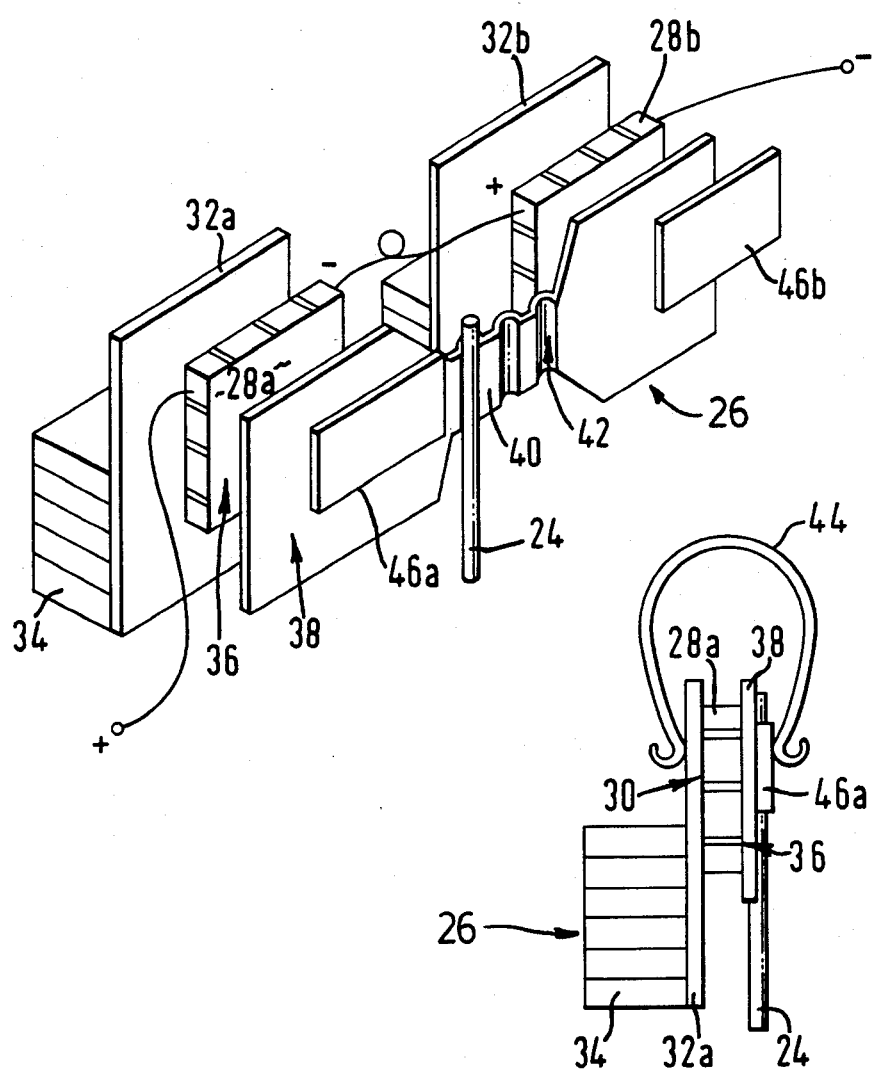
FIGS. 4a and 4b are perspective and side views respectively of a first embodiment of cooling apparatus in accordance with the present invention.

Referring now to FIGS. 4a and 4b, there is shown therein a first embodiment of the Peltier-effect type cooling device 26. Two Peltier-effect modules 28a and 28b are here connected in series to a suitable dc power supply source (not shown). Although a series electrical connection is shown, the modules could alternatively be connected in parallel or in some compound arrangement. Also, although in the preferred embodiment a pair of Peliter modules are used, one could alternatively use just a single such module. Each module comprises a series of p and n doped, bismuth telluride type limbs arranged in series so as to create a cold junction and a hot junction. The "hot" face 30 of each module 28a, 28b is covered with a suitable heat transfer compound, for example a grease, and a pair of heat sink plates 32a and 32b are secured respectively on the hot face of each module. Each of the heat sink plates 32a, 32b is equipped with fins 34 to enable the heat transferred to the heat sink plates to be dissipated into the working chamber 12 in such a way that the temperature/time profile set by the temperature programmer/controller unit 14 is maintained. The "cold" faces 36 of the Peltier-effect modules 28a, 28b are also covered with a suitable heat transfer compound, such as a grease, and a conductive metal strip or plate 38 is mounted so as to connect these two cold faces 36. As shown in FIG. 4a, the conductive metal strip 38, which may be for example of copper, aluminium or some similar high conductivity material has three separate areas. These consist of a pair of end plates in contiguous and overlapping relationship with the respective modules 28a and 28b, and a central bridging strip 40 of reduced width. This bridging strip 40 is provided with one or more corrugations or indentations 42 which are shaped to accommodate the sample container 24 with surface-to-surface contact. The provision of such corrugations 42 allows an increased surface area contact between the strip 40 and the container 24, and is particularly suitable for containers 24 having poor thermal conductivity, for example glass or thick-walled plastics containers. A spring clip or clamp 44 is provided across the device to clamp the container or containers 24 on to the conductive strip 40. The distance apart at which the Peltier modules 28a and 28b are set is determined by the dimensions required to accommodate the container or containers 24 on the strip 40. Two thermal insulating plates 46a and 46b are provided on the respective wing portions of the conductive strip 38 on the faces thereof which are opposite those faces which are in contact with the modules 28a and 28b. Although in the preferred embodiment the sample container 24 is in direct surface-to-surface contact with the conductive strip 38, 40, one could simply have the container spaced slightly from the strip or from a "cold" face, thereby maintaining thermal contact but not necessarily surface contact. Also of course, the sample container could be horizontal rather than vertical, and simply laid on the strip or "cold" face.

FIGS. 5a and 5b show a slightly modified arrangement in which the central bidging portion 40 of the conductive strip 38 is not indented or corrugated but is flat. This embodiment, where there is a reduced surface-to-surface contact between the sample container 24 and the bridging portion 40 of the strip 38, is suitable for containers 24 which have a low thermal mass, for example plastics straws or metal containers. It will be appreciated that other configurations of conductive strip can be devised to match the requirements of particular shapes of container, and particular container materials.

FIG. 6 shows an optical device which can be used in conjunction with the controlled cooling device of the present invention to detect the phase change from the liquid state to the crystalline state. A light beam from a light source 50 is transmitted through the sample container 24 towards a receiver 52. When the sample within the container 24 is in the liquid state the liquid beam will be detected by the receiver 52, but when there is a change to the crystalline state upon freezing, or upon the creation of a precipitate or sediment within the container, the light beam will be attenuated or completely blocked and the receiver 52 will detect this change. This detector can be linked up to the programmer/controller unit 14 so that the additional cooling introduction by the Peltier modules 26 is immobilised as soon as crystallization, precipitation or sedimentation has taken place. The term "light beam" used in relation to FIG. 6 is intended to include not only visible light but also other electromagnetic radiation which can be transmitted in the form of a beam. Again, other types of sensor than optical sensors could be used to detect the aforesaid phase change.

One preferred method of operation of the apparatus as hereinbefore described will now be given. The apparatus is set up with a specimen in a sample container 24 clamped to the conductive strip 38, 40. The Peltier assembly is mounted in the working chamber 12 of the freezer 10. A coolant, such as liquid nitrogen, is passed into the working chamber 12 through the inlet 18 to cause cooling of the specimen and container 24. Preferably, the sample container 24 is mounted so that one end of the container is in contact with the bridging portion 40 of the conductive strip, so that the local cooling effected by the strip is effected at one end of the container. Particularly when freezing biological specimens, it is desirable to initiate crystallization from one end of the container, preferably the upper end. Additionally, the Peltier assembly is spring-loaded within the cooling chamber to engage with the sample container 24 throughout the cooling process.

The degree of heat conduction between the sample container 24 and the strip 38, 40 is preferably first determined by initial experimentation, together with the measurement of the freezing point. Having thus determined the parameters of the particular system, the system can be set up for initiation of the local cooling by way of the Peltier device at preferably less than about 2° C. above the determined freezing point of the sample. The intention is to absorb heat locally around the upper surface of the liquid in the container 24 in order locally to induce seed crystals within the liquid. By matching the thermal masses of the cooling device and of the container 24 it is possible to achieve a carefully controlled initiation of these seed crystals. Preferably, the programmer/controller unit 14 (FIG. 1) is connected to the Peltier module 26 by a lead 54 and produces separate signal outputs at predetermined temperatures which are passed to the Peltier device 26 so that the Peltier device is actuated at a precise predetermined temperature.

When the temperature of the sample within the container 24 is close to the freezing point, an electric current is passed through the Peltier device, resulting in the cold faces 36 becoming colder and lowering the temperature of the conductive strip 38, 40. An electric current of for example 0.5 amps at 12 volts may in practice be passed through the Peltier modules when the specimen has reached the determined temperatures just above the critical crystallisation, precipitation or sedimentation point. The current is maintained for a period of for example 10 seconds in order to produce the necessary local cooling which will induce crystallization, precipitation or sedimentation at that part of the container which is in surface-to-surface contact with the strip 40. This crystallization, precipitation or sedimentation will then spread progressively through the whole of the specimen as the temperature continues to fall due to the continuing presence of the surrounding coolant, whether boosted or not.

If an optical device as shown in FIG. 6 is used, then this will detect the phase change from the liquid state to the crystalline state in that part of the sample container wherein local cooling is initiated, and can be used to trigger the programmer/controller unit 14, for example to effect termination of the additional cooling by way of the Peltier device as soon as the local crystallization, precipitation or sedimentation is detected.

It will be appreciated that no mechanical movement is required to initiate the local cooling of the sample, and there is no need for the operator to interfere with the sample container itself during the cooling process. With the use of a microprocessor-type control unit as the programmer/controller unit 14, it is possible to programme this in such a way as to operate the Peltier device at a given preset temperature.

It is also advantageous to provide for vibration of the specimen during the cooling process. This can be achieved by mounting the whole assembly 24, 26 on a suitable vibrator mounted either outside or within the working chamber 12. The vibration of the specimen within the container 24 during the cooling process reduces the chance of local supercooling of the sample. This also makes it easier to predict the crystallization point.

It is emphasised that in its broadest aspect the present invention is concerned with affecting or modifying the rate of cooling of a specimen. The method and apparatus of the invention are therefore appropriate also for the absorption of the heat of an exothermic reaction occurring during a cooling process, even if no crystallisation, precipitation or sedimentation occurs at that point in the cooling process.

I claim:

1. A method of modifying the cooling rate of an article which comprises a container at least partially filled with contents at least partially of liquid form and constituting a finite specimen, which comprises the steps of progressively cooling the specimen as a whole down to, through and below a given critical temperature for that specimen, and at a temperature level which is close to and above said critical temperature subjecting the specimen to supplementary cooling at only a localized part of the specimen by passing an electric current through Peltier effect means in thermal contact with only said localized part of the specimen, and triggering the initiation of said supplementary cooling by the specimen reaching said predetermined temperature level.

2. A method in accordance with claim 1, in which the speciman is elongate in shape and the supplementary cooling is effected at one end of the specimen.

3. A method in accordance with claim 1, in which said given critical temperature is the freezing point of the liquid.

4. A method in accordance with claim 1, in which the supplementary cooling is initiated at less than about 2° C. above said critical temperature.

5. A method in accordance with claim 1, in which the general cooling of the specimen is effected by a controller according to a predetermined temperature/time profile, and the initiation of the supplementary cooling is effected automatically by said controller.

6. A method in accordance with claim 1, which includes vibrating the specimen during the cooling process.

7. A method in accordance with claim 1, which includes sensing a change in the specimen from the liquid phase to an at least partially crystalline or solid phase.

8. A method in accordance with claim 7, which includes triggering a cessation of the supplementary cooling in response to the sensing of said change.

9. A method in accordance with claim 1, in which said supplementary cooling is accompanied by or followed by a boost in the external cooling of the specimen.

10. A cooling device for modifying the cooling rate of a specimen which is at least partially of liquid form, comprising first cooling means arranged to be connected to an electric power source and to function in accordance with the Peltier effect to provide a surface at which heat is absorbed thereby to cool said surface, a container at least partially filled with contents constituting a finite specimen and positioned so that only a localized portion thereof is in thermal contact with said surface, second cooling means for progressively cooling the specimen as a whole down to, through and below a given critical temperature for the specimen, sensor means providing an output responsive to the temperature of the specimen, and control means operative, in response to a signal from said sensor means, to initiate energization of said first cooling means to supplement said second cooling means at a temperature which is close to and above said given critical temperature for said specimen.

11. A cooling device in accordance with claim 10, in which said cooling means comprises two Peltier effect modules each having a surface at which heat is absorbed, and thermally conductive means interconnecting said surfaces and with which the specimen container is in thermal contact.

12. A cooling device in accordance with claim 11, in which said thermally conductive means comprises a metallic strip with the specimen container arranged to be maintained in contact with a central portion of the strip bridging end portions of the strip which are in contact with said module surfaces.

13. A cooling device in accordance with claim 12, in which said central bridging portion has a surface which is shaped to match the configuration of that part of the specimen container which is maintained in contact with said surface.

14. A cooling device in accordance with claim 13, in which said bridging portion surface is corrugated to provide at least one semi-cylindrical surface for contact with the container.

15. A cooling device in accordance with claim 11, in which the Peltier effect modules are provided with heat dissipation means on surfaces opposed to those at which heat is absorbed.

16. A cooling device in accordance with claim 10, which includes means to vibrate at least the specimen container.

17. A cooling device in accordance with claim 10, which includes sensing means operative to detect a change in the specimen from the liquid phase to an at least partially crystalline or solid phase.

18. A cooling device in accordance with claim 17, in which said sensing means triggers said control means to de-energise said cooling means in response to the detection of such a change.

19. A cooling device according to claim 17, in which said sensing means comprises an optical sensor.

20. Cooling apparatus for cooling a specimen which is at least partially of liquid form, comprising a cooling device as claimed in claim 10, a working chamber within which said cooling device is positioned, means to supply a coolant to said working chamber, and temperature sensing means within said working chamber connected to said control means.

21. Cooling apparatus as claimed in claim 20, which includes vibrator means outside the working chamber for the vibration of at least the specimen.

22. Cooling apparatus as claimed in claim 20, in which said control means is programmed to energise said cooling means at a preset temperature.

* * * * *